United States Patent [19]

Oré et al.

[11] 4,132,760

[45] Jan. 2, 1979

[54] HEMIHYDRATE TYPE PHOSPHORIC ACID PROCESS USING REDUCED PRESSURE

[75] Inventors: Fernando Oré, Whittier; John D. Ellis, Upland; James H. Moore, La Verne, all of Calif.

[73] Assignee: Occidental Petroleum Corporation, Los Angeles, Calif.

[21] Appl. No.: 703,208

[22] Filed: Jul. 7, 1976

[51] Int. Cl.$^2$ .................. C01F 1/00; C01F 5/00; C22B 26/20; C01B 25/16
[52] U.S. Cl. .................................. 423/167; 423/320
[58] Field of Search ............... 423/167, 319, 320, 555

[56] References Cited

U.S. PATENT DOCUMENTS

| | | | |
|---|---|---|---|
| 1,836,672 | 12/1931 | Larsson | 423/167 |
| 2,968,544 | 1/1961 | Zeitz et al. | 423/320 |
| 3,257,168 | 6/1966 | Chelminski | 423/167 |
| 3,416,889 | 12/1968 | Caldwell | 423/167 |
| 3,418,077 | 12/1968 | Robinson | 423/167 |
| 3,453,076 | 7/1969 | Long et al. | 423/167 |
| 3,522,003 | 7/1970 | Lopker | 423/167 |
| 3,522,004 | 7/1970 | Lopker | 473/167 |
| 3,690,826 | 9/1972 | Hasken | 423/370 |
| 3,939,248 | 2/1976 | Caldwell | 423/167 |

FOREIGN PATENT DOCUMENTS 1959122  5/1971  Fed. Rep. of Germany ........... 423/319

OTHER PUBLICATIONS

Slack–Phosphoric Acid–1968, pp. 383 to 385.

*Primary Examiner*—O. R. Vertiz
*Assistant Examiner*—Eugene T. Wheelock
*Attorney, Agent, or Firm*—Barry A. Bisson; Edward A. Grannen, Jr.; W. G. Lane

[57] ABSTRACT

Phosphate rock and sulfuric acid are reacted under conditions which result in the formation calcium sulfate hemihydrate and phosphoric acid of about 30% to about 55% $P_2O_5$. A two vessel reaction system is used in which the reaction slurry undergoes inter- and intra-vessel circulation. This results in excellent dispersion of reactants and minimization of temperature and concentration gradients throughout the slurry.

9 Claims, 3 Drawing Figures

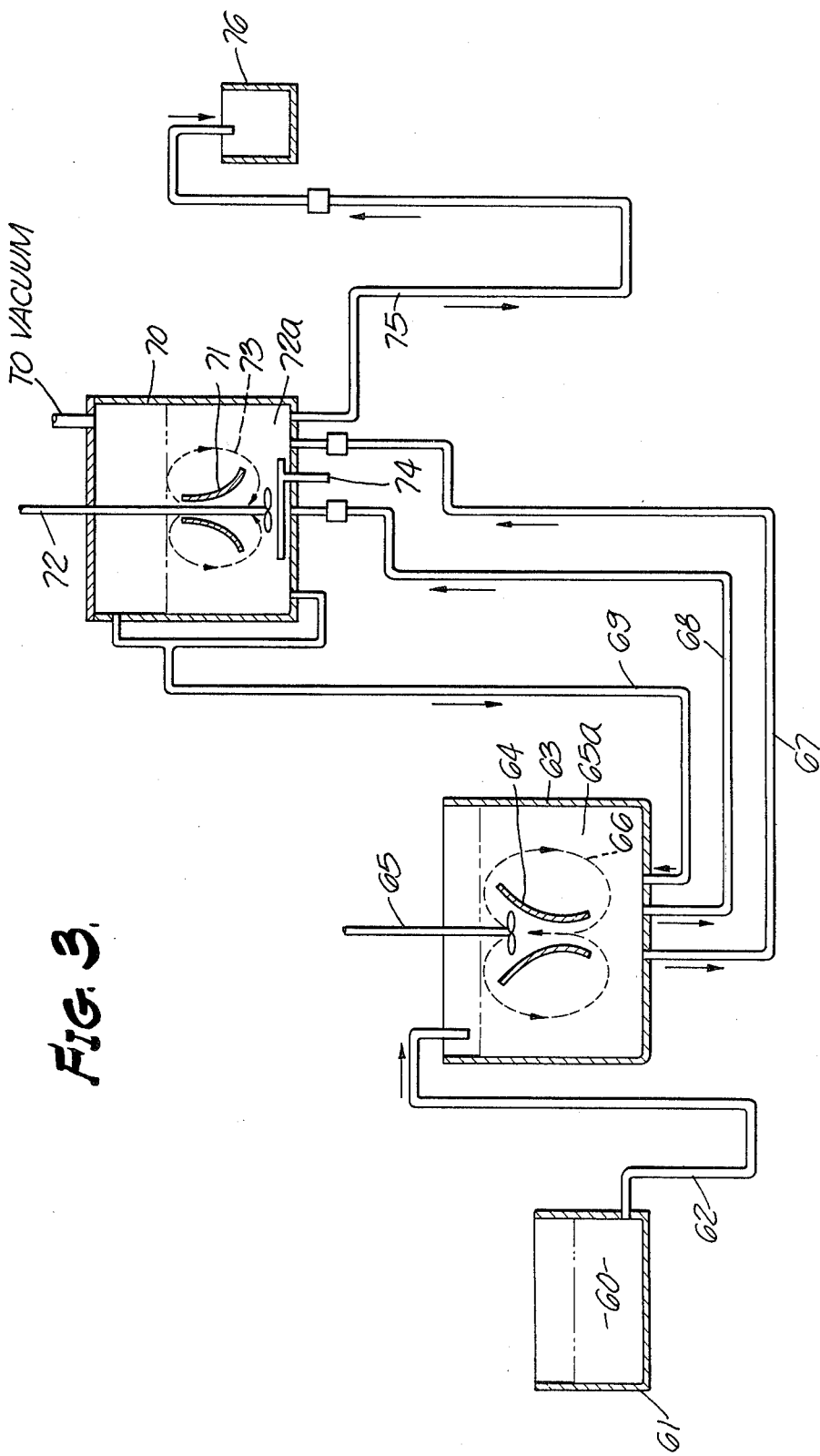

HEMIHYDRATE TYPE PHOSPHORIC ACID PROCESS USING REDUCED PRESSURE

SUMMARY

The present invention is directed to the manufacture of phosphoric acid by the wet process. The hemihydrate, or as it is sometimes called the semihydrate, process is employed to produce wet process phosphoric acid from phosphate rock and sulfuric acid. Phosphate rock and phosphoric acid are added to a first reaction vessel which contains a first slurry comprising calcium sulfate hemihydrate, monocalcium phosphate, sulfuric acid and phosphoric acid. The phosphate rock is substantially converted into monocalcium phosphate, phosphoric acid and calcium sulfate hemihydrate in the first reaction vessel. The soluble sulfate content of the first slurry in the first reaction vessel is maintained at a concentration of about +0.7% to about −4%. Sulfuric acid is added to the second reaction vessel which contains a second slurry comprising calcium sulfate hemihydrate, monocalcium phosphate, sulfuric acid and phosphoric acid. The sulfuric acid reacts with the phosphate rock and the monocalcium phosphate producing calcium sulfate hemihydrate and phosphoric acid. The soluble sulfate concentration of the second slurry is maitained at a value of about +0.7% to about +4.5%; provided that the soluble sulfate content of the second slurry is about +1.0% or greater when the soluble sulfate content of the first slurry is +0.7%. Sulfuric acid is added in amounts such that the sulfate content of the added acid and the sulfate content of the added rock is equivalent to about 90% to about 100% of the stoichiometric amount of sulfate required to react with calcium added in the phosphate rock to form calcium sulfate hemihydrate. In order to maintain the desired soluble sulfate concentration in the first reaction vessel and in the second reaction vessel, circulation between the two reaction vessels is initiated. A first portion of the first slurry from the first reaction vessel is circulated through a first conduit into the second reaction vessel, and a first portion of the second slurry from the second reaction vessel is circulated through a second conduit into a first reaction vessel. This circulation is continuous. In order to better disperse the added phosphate rock and the added sulfuric acid within the slurry of the first and the second reaction vessels respectively and to better disperse the incoming slurry with the slurry present in the given reaction vessel, a second portion of the first slurry and a second portion of the second slurry is circulated within the first and second reaction vessels respectively each through its own draft tube at a rate equal to at least 50% of the volume of the slurry in a given reaction vessel per minute. This inter- and intravessel circulation disperses the reactants within the slurry in the respective reaction vessels. A third portion of the second slurry is removed from the reaction system so as to separate the liquid and solid components from the said slurry.

BACKGROUND

The present invention is directed to a process for the production of phosphoric acid by the wet process. The invention is directed to the production of phosphoric acid by the calcium sulfate hemihydrate or simply the hemihydrate process. The present invention is directed to the process in which the control of reactant concentrations is improved, a concentrated phosphoric acid (about 30% to about 55% $P_2O_5$) is produced, a reduction in sulfuric acid usage is realized and a substantial reduction in electrical energy consumption is also realized.

Phosphoric acid has been prepared by the wet proess for many years. The wet process involves the reaction of phosphatic solid materials, hereinafter termed phosphte rock, with sulfuric acid. A slurry comprising calcium sulfate, monocalcium phosphate, phosphoric acid and sulfuric acid is the usual reaction media. The names of the three processes for the production of phosphoric acid by the wet process are based on the by-product calcium sulfate produced; namely, the gypsum or dihydrate process, the hemihydrate process, and the anhydrite process. The type of by-product is dependent upon the temperature of the system and the $P_2O_5$ concentration of the liquid phase of the slurry. Other factors such as fluorine concentration, alumina concentration, and sulfuric acid concentration play a less important role.

Gypsum, $CaSO_4 \cdot 2H_2O$, is the by-product formed when the wet process is run at a temperature of 90° C. or less and a $P_2O_5$ concentration of about 30% in the liquid portion of the slurry. Increasing the temperature to about 80°–120° C. and the $P_2O_5$ concentration to about 40% in the liquid phase will yield hemihydrate, $CaSO_4 \cdot \frac{1}{2}H_2O$. Adjusting the temperature and the concentraions, for instance, to 75° C. and 40% $P_2O_5$ results in a mixture of gypsum and hemihydrate which is very unstable. An unstable system such as this causes trouble during filtration due to the hardening or setting up of the gypsum-hemihydrate solid on the filter. Care must be exercised in maintaining the proper temperature and $P_2O_5$ concentrations in the process being run in order to avoid such problems. $CaSO_4$ anhydrite is produced at temperatures of about 130° C. and $P_2O_5$ concentrations greater than 30%. This latter process is most difficult to run due to severe corrosion at the higher temperatures and the instability of the anhydrite during processing.

Several problems are inherent in the production of phosphoric acids by the wet process. The degree to which these problems affect the three process will vary due to the different operating conditions employed. Several problems which affect recovery and/or processing of the phosphate rock during the production of phosphoric acid are discussed below.

Phosphate values can be lost during processing of phosphate rock by several different mechanisms. The first consists of the coating of the phosphate rock with calcium sulfate. This impeeds and/or inhibits the recovery of the phosphate values from the rock, hence resulting in very low yields. The second consists of substitution of calcium phosphate within the calcium sulfate lattice. The substituted phosphate values cannot be recovered by washing during the separation stage and hence pass to waste. This again results in poor recovery from the phosphate rock. The third problem involves the rapid precipitation or crystallization of many very small crystals of calcium sulfate. This lads to very poor filtration and filterability. The conditions which are employed in the three wet processes are listed and their effects on the recovery of $P_2O_5$ from the rock.

As the $P_2O_5$ concentration of the liquid portion of the reaction slurry increases (about 28% $P_2O_5$ for the dihydrate process; about 40% $P_2O_5$ for the hemihydrate process and about 50% $P_2O_5$ for the anhydrite process), there is a great tendency to increase the substitution of calcium phosphate within the calcium sulfate crystal lattice. This results from the increase in $HPO_4^{-2}$ concentration in the liquid portion of the slurry. In the same manner the increase in the $P_2O_5$ concentration of the liquid portion of the slurry tends to increase the viscosity of the reaction media and hence also tends to increase the amount of substitution of the phosphate within the calcium sulfate crystal structure due to reduced diffusion of the $HPO_4^{-2}$ species within the slurry. If, however, the temperature is increased, as occurs from going from the dihydrate process to the hemihydrate process, the viscosity of the reaction media is lower and hence the degree of substitution of the calcium phosphate within the calcium sulfate crystal structure is decreased. It must be recognized, however, that there are temperature limitations which must be observed for the process under consideration.

Increasing the sulfate concentration in the liquid phase of the slurry results in a decrease in the calcium ion concentration, thus tending to decrease the amount of substitution of calcium phosphate within the sulfate crystal lattice. However, care must be exercised not to increase the sulfate concentration to such an extent that the dissolution or the recovery of phosphate values from phosphate rock is impeded by the coating of the rock with a layer of calcium sulfate. Excess sulfate concentration in the presence of high localized concentrations of calcium ions results in the precipitation of many very small crystals of calcium sulfate, resulting in a slurry difficult to filter. Thus the sulfate concentration can act both to increase the recovery of phosphate from the phosphate rock, or it can result in reduced recoveries of phosphate from the phosphate rock with attendant reduced filtration rates.

An increase in solids in the slurry will tend, in general, to increase crystal growth of the calcium sulfate formed by the reaction of calcium ions with sulfate ions. This will tend to result in larger crystals which will be more easily filterable and washable. In general, the variation of the solids content results only in very small variations in the degree of substitution of calcium phosphate within the calcium sulfate crystal lattice. In addition, it is imperative not to increase the solids to such an extent that the viscosity of the slurry is increased to such an extent that mixing becomes very difficult and localized supersaturation occurs.

Thorough mixing is very desirable whether running the dihydrate, the hemihydrate or the anhydrite process. Good mixing will decrease the localized high concentration of the reactants; namely, the calcium phosphate and the sulfuric acid. Decreasing such localized concentrations, results in a lowering of the substitution losses, a lowering of losses due to coating the rock and an improvement in the crystallization conditions.

Thus, it is observed that a change of one variable may favorably affect the recovery of $P_2O_5$ from phosphate rock employing one of the wet process methods and it may be detrimental to the recovery of $P_2O_5$ employing a different process. Therefore it is necessary to choose the combination of process variables which will result in the best recovery of $P_2O_5$ from the phosphate rock along with acceptable filterability of the resulting slurry for the process at hand.

The recovery of the phosphate values from the phosphate rock can be greatly increased if the agitation or mixing is maintained at a high level. Previous workers in the field have directed their energy to achieve maximum mixing in the wet process. As a result of this activity, today there are one vessel and multi- vessel systems in use for the production of phosphoric acid by the wet process. The purpose is to achieve maximum mixing so as to increase the recovery of the phosphate values from the phosphate rock and to have the best environment for dissolution of the rock and for crystallization of $CaSO_4$.

In a one vessel process, the phosphate rock and the sulfuric acid are added to the slurry in one tank. Agitators, in union with baffles, are used to circulate the slurry into which the reactants (phosphate rock and sulfuric acid) are added. To the extent that the localized concentration differences are minimized, the slurry has only one sulfate level. This is undesirable, since the phosphate rock should preferably be dissolved at a low sulfate concentration whereas crystallization should occur at a high sulfate concentration.

A multi-vessel system can be of two types. Two or more compartments or cells can be constructed within one vessel, the compartments being interconnected in series. The reactants are added separately, that is, in different compartments in order to increase the dispersion of said reactant in the slurry prior to reacting with the other reactant. At the last compartment, some slurry is removed from the system for recovery of phosphoric acid; the major portion of the slurry being recycled to the first compartment.

Multi-vessel processes involve the use of two or more vessels connected in series, the reactants are added to the slurry in separate vessels so as to more completely disperse one reactant in the slurry before it is contacted by the later added reactant(s). Again the system is arranged so that a portion of the slurry is recycled from a later reactor back to the first reactor.

The reaction between sulfuric acid and phosphate rock is exothermic. In order to control the temperature of the reaction system, provisions must be made to remove this excess heat. Previously this has been accomplished by (1) blowing air through the slurry or (2) pumping a portion of the slurry to a vessel under vacuum or (3) conducting the operation in a vessel under vacuum.

The use of air as a coolant is not too desirable because it is necessary to scrub large amounts of air exiting the system to remove pollutants, mainly fluorine in the form of hydrogen fluoride or silicon tetrafluoride. The equipment required is quite expensive. When a portion of the hot slurry is removed from the main body of the slurry, and subjected to vacuum, cooling occurs by the evaporation of water (U.S. Pat. No. 2,699,985). The cooled slurry is then added to the main body of the hot slurry and moderates the temperature of the process.

The method of conducting the reaction under vacuum has many desirable features. The cooled slurry is immediately dispersed within the hot slurry and temperature differentials within the slurry are minimized. The slurry is concentrated by the removal of water, and the desired temperature is easily maintained. The above described multi- compartment and multi- vessel systems improved on dispersing the reactants to some extent, however, greater dispersion of the reactants is desirable in order to improve the dispersion of the reactants in a one vessel reactor. Caldwell, U.S. Pat. No. 3,415,889 and 3,939,248 and Bergstrom, U.S. Pat. No. 3,666,143 and 3,917,457 developed a combination reactor-cooler which is fitted with a draft tube. The vessel was maintained under a vacuum while the slurry was circulated within a vessel. Using the draft tube with an agitator it is possible to circulate the slurry at such a flow rate that upwards of 200% of the volume of the slurry is circulated through the draft tube per minute, constantly renewing the surface of the slurry exposed to the vacuum. With this type of circulation, dispersion of the reactants is improved over the conventional one vessel system. In addition to better dispersion of the reactants, the slurry on exposure of the vacuum at the surface is cooled by evaporation of water. The temperature differential within the system is minimized by the rapid flow rate realized. The cooled slurry is immediately mixed with the hot slurry minimizing the localized cooling affect.

Lopker, U.S. Pat. No. 3,522,003 and 3,522,004 describes a two vessel system for the production of phosphoric acid from phosphate rock and sulfuric acid. These processes involve passing a slurry of phosphoric acid and calcium sulfate through a circuit which contains two vessels in series, at least one of which is under vacuum. The vacuum applied to one vessel cools the slurry by evaporation of water. The cooled slurry is then rapidly dispersed within the system minimizing cooling effects and preventing supersaturation of the calcium sulfate due to reduced temperatures. The levels of the slurries within the two vessels are vertically offset.

Sulfuric acid, phosphoric acid, phosphate rock or a mixture of phosphoric acid-phosphate rock can be added to the slurry in different vessels. The reactants are mixed in the vessel and are circulated from one vessel to another. In this way localized high concentrations of the added reactants are minimized. Good recovery of $P_2O_5$ values from the rock are realized. Better filtration rates are also obtainable due to the retardation of the formation of excessive number of very small calcium sulfate crystals resulting from supersaturation.

Processes for the production of phosphoric acid by the hemihydrate process are well known in the art. A. V. Slack, in "Phosphoric Acid" Part One, Marcel Dekker, Inc., New York, 1968, describes hemihydrate process. The problems encountered are observed in filtering the hemihydrate slurry and the high degree of substitution of phosphate in the calcium sulfate lattice. Attempts to overcome the deficiency in filtration rate and poor $P_2O_5$ recoveries while maintaining the production of phosphoric acid containing about 40% $P_2O_5$, resulted in the development of a hemihydrate-dihydrate system. U.S. Pat. No. 3,472,619 and 3,552,918 are representative of the systems of the systems employed.

These patents describe the preparation of phosphoric acid by the hemihydrate process, recovering said phosphoric acid from the solid $CaSO_4 . \frac{1}{2} H_2O$, recrystallization of $CaSO_4 . \frac{1}{2}H_2O$ to $CaSO_4 . 2H_2O$, and the recovery of phosphoric acid liberated during the recrystallization of $CaSO_4 . 2H_2O$. Apparently, the best of both processes is achieved. High concentration, about 40% $P_2O_5$ acid is recovered while low losses in the filter cake are observed as the result of the recrystallization of the $CaSo_4 . \frac{1}{2} H_2O$.

Fitch (U.S. Pat. No. 3,552,918) describes a process for the production of concentrated phosphoric acid and gypsum including the acidulation of phosphate rock in a first zone in which the resulting slurry contains from about 1% ($-2.45\%$ $SO_4^=$) to about 4.5% ($-11\%$ $SO_4^=$) excess calcium. The slurry produced in the first zone is then transferred to a second zone in which an excess of sulfuric acid is present such that from about 3% to about 6% excess sulfuric acid is present in the slurry. Hemihydrate initially produced is converted to gypsum.

Long (U.S. Pat. No. 3,453,076), Peet (U.S. Pat. No. 2,885,264) and Robinson, (U.S. Pat. No. 3,418,077) described processes for the production of phosphoric acid by the hemihydrate process. No additional recrystallization of the $CaSO_4 . \frac{1}{2}H_2O$ is required in these processes. In the Robinson process phosphoric acid containing from about 40% to about 55% $P_2O_5$ by weight is produced. This process which comprises in a first stage reacting in the presence of excess calcium ions, phosphate rock with at least nine parts by weight of phosphoric acid for each part of calcium added, said phosphoric acid containing at least 37% by weight $P_2O_5$ and 1% to 3% by weight dissolved sulfate whereby the phosphate rock is converted into a slurry comprising monocalcium phosphate, phosphoric acid, and calcium sulfate, the percentage of calcium ion precipitated as calcium sulfate being 10 to 60%, preferably 20–50% by weight of total calcium fed, in a second stage reacting the slurry from the first stage with sulfuric acid whereby phosphoric acid containing at least 40% $P_2O_5$ by weight and calcium sulfate hemihydrate is formed, the sulfuric acid being used in an amount 0.5 to 2.0% by weight in excess of that required to convert the calcium content of the phosphate rock fed to the first stage into calcium sulfate, and in the third stage separating the phosphoric acid from the calcium sulfate and washing the crystals. The temperature of the first and second stages being in the range from 80 to 115° C., preferably from 90–110° C.

BRIEF DESCRIPTION OF THE DRAWINGS

In FIG. I, a schematic of the preferred embodiment of the process is shown;

In FIG. II, a schematic of another embodiment of the process is shown; and

Figure 1:
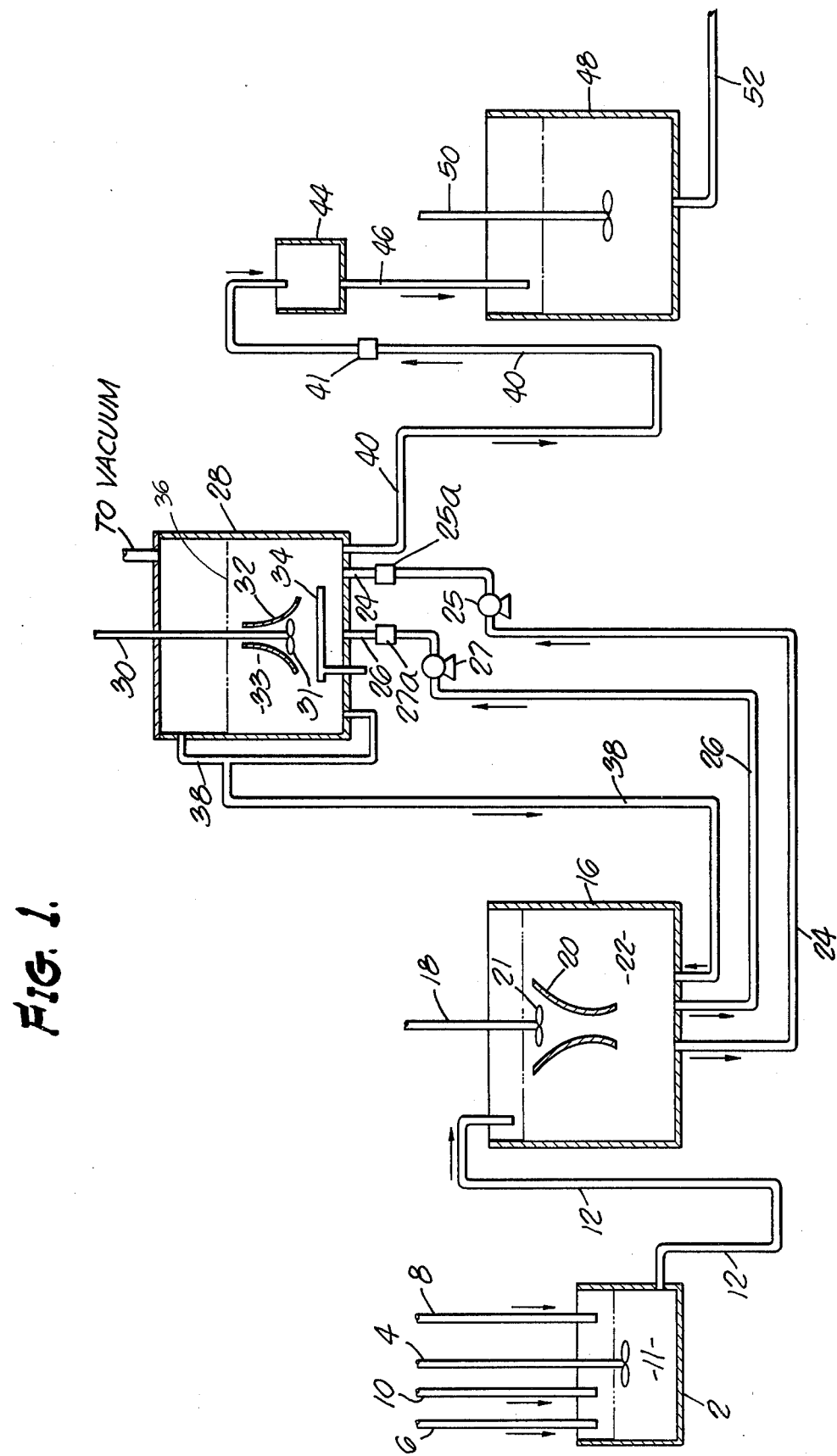
Figure 2:
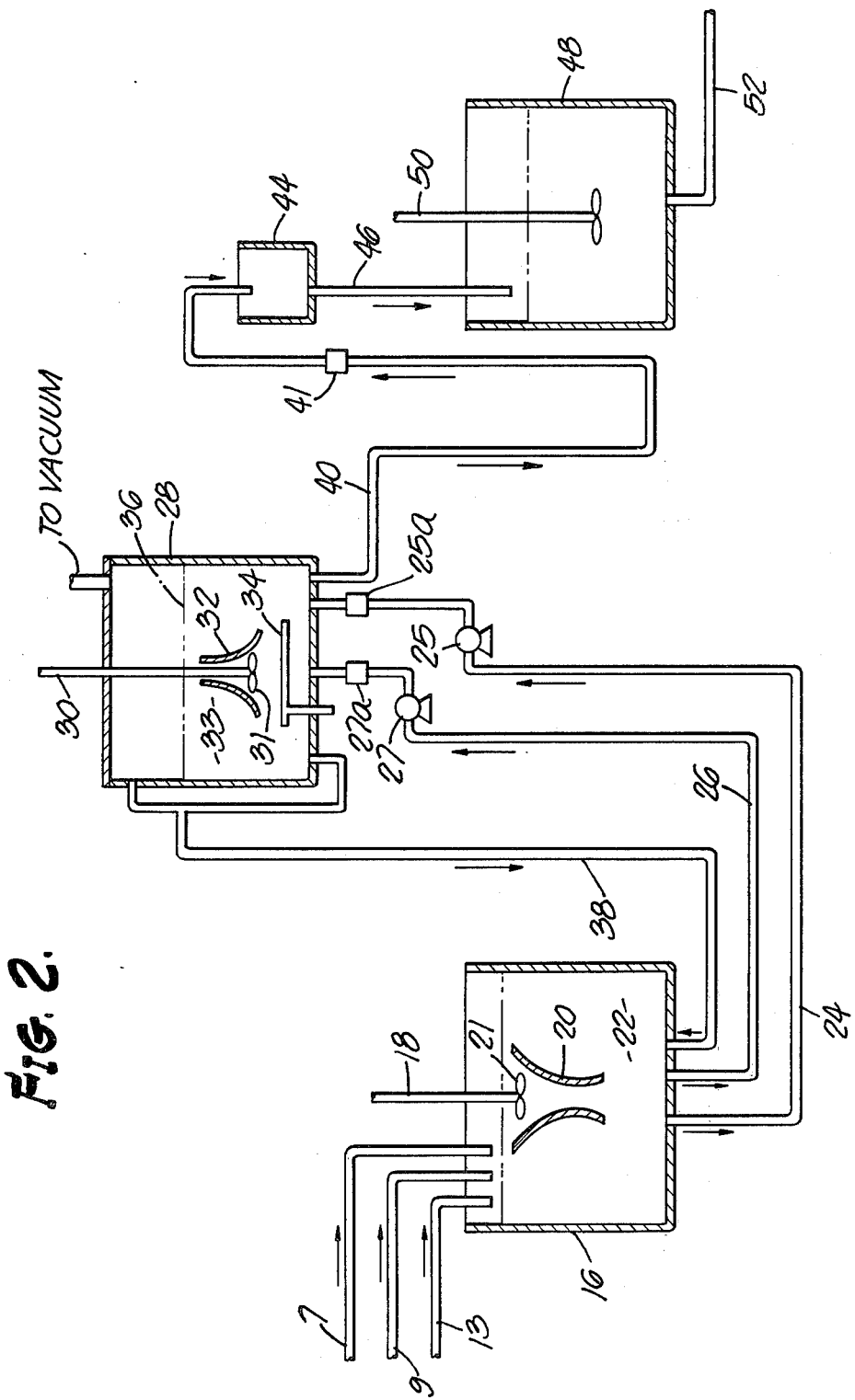

In FIG. III, a schematic of the inter- and intra- vessel flow patterns are shown.

DETAILED DESCRIPTION

This invention is directed to a process for the production of phosphoric acid by the calcium sulfate hemihydrate process.

Phosphate rock, either calcined or uncalcined, and phosphoric acid are added to a first slurry of, calcium sulfate hemihydrate, monocalcium phosphate, phosphoric acid and sulfuric acid. Preferably, the phosphate rock is slurried in the phosphoric acid prior to the addition to the first slurry. Phosphate rock, about 95% of +100 mesh, containing at least 32% $P_2O_5$ is the preferred source of phosphate for the process. Ground or unground rock can be used. However, phosphate rock of 95% of −200 mesh can be used. Rock containing less than 32% $P_2O_5$ is acceptable, and can be employed in this process. High alumina phosphate pebble may also be used. The phosphate rock is slurried in phosphoric acid that contains from about 13% to about 47% $P_2O_5$. Phosphoric acid, recycled from the separation section, containing from about 13% to about 47% $P_2O_5$ is usually used in the process. However, phosphoric acid from other sources, such as other phosphate plants, merchant grade acid may be used. When the phosphoric acid is recycled from the separation section it will usually contain from about 0.5% to about 3.5% sulfuric acid by weight.

The temperature of the phosphate rock-phosphoric acid mixture is maintained at about 50° C. to about 100°

C., preferably from about 90° C. to about 100° C. The resulting mixture is from about 30% to about 40% solids by weight, about 33% being preferred. A defoamer is added if and when required. Various antifoam agents can be used, including tall oil fatty acids, oleic acid, sulfated tall oil fatty acids, sulfated oleic acid, silicones and reaction products of amines and carboxylic acids.

The phosphate rock-phosphoric acid mixture is added to a first slurry of, calcium sulfate hemihydrate, phosphoric acid monocalcium phosphate and sulfuric acid in a first reaction vessel. The phosphate rock and phosphoric acid may be added separately to the first slurry in the first reaction vessel. The phosphate rock-phosphoric acid mixture on being added to the first slurry in the first reaction vessel is immediately dispersed within the first slurry. A first portion of the first slurry is transferred to a second reaction vessel.

The first reaction vessel is fitted with a draft tube and an agitator. (The agitator consists of a shaft fitted with a propeller at the bottom thereof). The agitator is so located with respect to the draft tube that on activation of the agitator, a second portion of the first slurry is drawn from the bottom of the draft tube up through the draft tube and out the top of the draft tube. On exiting the draft tube said slurry passes in a downward direction in the space between the draft tube and the walls of the first reaction vessel. The direction of circulation through the draft may be reversed and is not critical. Circulation is thus established within the first reaction vessel. The rate at which said slurry is circulated is at least equal to about 50% of the volume of the slurry in the first reaction vessel per minute, preferably from about 50% to about 150% and most preferably about 100%. This circulation thoroughly disperses the phosphate rock-phosphoric acid mixture with the first slurry. The first slurry contains sulfuric acid which reacts exothermically with the phosphate rock being added. Dilution of the sulfuric acid also results in the evolution of heat. These exothermic reactions supply the heat required to maintain the temperature of the slurry in the first reaction vessel between about 66° C. to about 113° C. The soluble sulfate content of the of first slurry is maintained at about +0.7% to about −4%. [As measured, soluble sulfate values can be either positive or negative. Soluble sulfate values include not only the sulfuric acid present in the liquid component of the slurry but also the soluble calcium sulfate therepresent. Negative soluble sulfate values indicate that an excess of calcium ions are present in the solution as is usually observed in the phosphate rock-phosphoric acid mixture. Positive soluble sulfate values indicate that excess sulfate ions are present. A value of 0.0% indicates that the sulfate ions and the calcium ions are equivalent stoichiometrically within the limits of the analysis.] The residence time of the solids in the first reaction vessel is from about 2.0 hours to about 5.0 hours, preferably from about 2.5 hours to about 4.5 hours.

A first portion of the first slurry is transferred through a first conduit into a second reaction vessel. The second reaction vessel which can be subjected to a vacuum, is fitted with a draft tube, an agitator and a sulfuric acid inlet. The agitator consists of a shaft fitted with a propeller at the bottom thereof. The shaft and agitator are so located with respect to the draft tube that on actuation of the agitator a second portion of the second slurry is caused to flow from the bottom of the draft tube up through the draft tube and out the top of the draft tube. On exiting the draft tube, said second portion of the second slurry flows in a downward direction in a space between the draft tube and the inside walls of the second reaction vessel. The direction of the circulation can be reversed and is not critical. The rate at which the slurry is circulated is at least equal to about 50% of the volume of the slurry in the vessel per minute, preferably from about 50% to about 150% of the volume and most preferably about 100% of the volume. Sulfuric acid, preferably about 98%, is added through the sulfuric acid inlet into the second slurry either as is or mixed with phosphoric acid. The first portion of the first slurry is also added into the second slurry. A crystal modifier, usually a derivative of an organic sulfonic acid, can be added to the slurry in the second reaction vessel. The organic sulfonic acid can be an alkyl-, aryl- or an alkylaryl- sulfonic acid or a sulfated derivative of an carboxylic acid. For example, tetradecyl sulfonic acid, benzene-sulfonic acid, isooctylbenzene sulfonic acid and sulfated oleic acid may be used as crystal modifiers in this process. The crystal modifier is added for the purpose of increasing the growth of the hemihydrate crystals formed in the system. The flow of the second slurry within the second reaction vessel thoroughly disperses the first portion of the first slurry, the sulfuric acid and the crystal modifier within the second slurry. (The location of the sulfuric acid inlet in the second reaction vessel is not critical. It may be at the top, the middle, the bottom or at intermediate points of the second reaction vessel. The sulfuric acid conduit attached to the sulfuric acid inlet may enter the second reaction vessel from the top, the bottom, or points intermediate therein, the exact point of entrance into the vessel is not critical.) Phosphoric acid, if needed, can be added to the second slurry within the second reaction vessel. The surface of the second slurry in the second reaction vessel is exposed to a pressure of between about 2 to about 29 inches of mercury absolute, preferably from about 3 to about 20 inches mercury absolute. Water and volatile components added to or produced in both the first and second slurries can be removed from the second slurry causing a reduction in the temperature of the second slurry from which the volatiles are removed. The cooled second slurry is thoroughly mixed so that temperature differentials are minimized within the total volume of the second slurry. With this evaporative cooling, the temperature of the second slurry is maintained between about 66° C. to about 113° C. preferably from 80° C. to about 105° C. [The process can be run while maintaining both the first and second reaction vessels at atmospheric pressure.] Sulfuric acid which is added to the second slurry in the second reaction vessel through the sulfuric acid inlet can be from about 89% to 99% $H_2SO_4$ or more, preferably about 98% $H_2SO_4$.

It has been determined that the total sulfate value added to the system is the sum of the sulfate values in sulfuric acid added plus the sulfate values added in the rock and this total is only about 90% to 100% of the stoichiometric amount of sulfate needed to convert the calcium added in the rock fed to the first reaction vessel into calcium sulfate hemihydrate. See Table 1 for the compilation of sulfuric acid usage. Listed are the tons per day (TPD) of phosphate rock fed, % CaO in the rock, % $SO_4^=$ in the rock, CaO fed (TPD), stoichiometric sulfate for the calcium in the rock (TPD), sulfate in sulfuric acid fed to the unit (TPD), sulfate equivalent in the rock (TPD), the total sulfate used (TPD), and total sulfate used as a fraction of the stoichiometric amount of sulfate required for the calcium in the rock. The soluble sulfate content as measured in the second slurry should be from about +0.7% to about +4.5%, preferably from about 2.5% to about 3.5%; provided that when the soluble sulfate content of the first slurry is about +0.7% then the soluble sulfate content of the second slurry must be +1.0% or more. The specific gravity of the slurry in the second reaction vessel is about 1.80 ± 0.2 g/cc. The specific gravity of the liquid portion of the slurry is about 1.56 ± 0.20 g/cc. The liquid gravity corresponds to a phosphoric acid which contains about 42% ± 12% $P_2O_5$. Residence time of the solids in the second reaction vessel is from about 0.6 hour to about 2.0 hours, preferably from about 0.7 hour to about 1.6 hours.

The excellent mixing obtained with this system is achieved using approximately 1/10 of the horsepower required for a comparable wet process phosphoric acid plant such as a Dorr-Oliver or a Prayon Plant.

A first portion of the second slurry flows from the second reaction vessel back to the first reaction vessel through a second conduit and is thoroughly dispersed within the first slurry. It is the flow of the second slurry to the first slurry which aids in controlling the temperature of the first slurry and adds sulfate values (sulfuric acid) and phosphoric acid values to the first slurry in order to dissolve the rock. Additional sulfate values are added to the first slurry in the first reaction vessel with the recycled phosphoric acid. Circulation between vessels and within vessel minimizes localized concentration of reactants of hot slurry and of cooled slurry thus resulting in a more easily controlled process than previously observed. A third portion of the second slurry is removed from the second reaction vessel and is transferred through a conduit to a reservoir. The third portion of the second slurry, on a weight basis, is approximately equal to the phosphate rock, the phosphoric acid, and the sulfuric acid added in the first and second reaction vessels respectively minus the volatiles (on a weight basis) removed from the second reaction vessel which can be subject to a vacuum. The third portion of the second slurry is constantly stirred in the third vessel to prevent separation of the solids from the liquid and is maintained at about 66° C. to about 113° C., preferably from about 70° C. to about 100° C. The residence time in the third vessel is relatively short, being from about 0.5 hour to about 1.5 hours, preferably from about 0.60 hour to about 1.25 hours. The soluble sulfate concentration of the slurry in the third vessel may change somewhat due to continued reaction of the soluble sulfate values with any calcium values therepresent. Sulfuric acid may be added to the third vessel to adjust the sulfate values.

From the third vessel, the slurry is transferred to the separation section in which the slurry is separated into its solid and liquid components using apparatus well known in the art.

Slurry samples are removed from the system at several locations. A sample port is placed in the first conduit at a location between the first and second vessels, the distance between the first and the second reaction vessel is not critical. Slurry removed from this sample port represents the first slurry. A sample port is located in the conduit between the second reaction vessel and the reservoir to which the third portion of the second slurry is pumped. The location of this sample port in terms of distance between the second reaction vessel and the reservoir is not critical. Slurry samples obtained

TABLE 1

| Rock Fed, TPD | CaO in Rock, % | $SO_4$ in Rock % | CaO Fed, TPD | Stoichiometric Sulfate ($SO_4^=$) for CaO in Rock TPD | Sulfate Present in 100% $H_2SO_4$ Fed to Unit, TPD | Sulfate Equivalent in Rock, TPD | Total Sulfate Used, TPD | Total $SO_4^=$ used as a fraction of Stoichiometric Amount |
|---|---|---|---|---|---|---|---|---|
| 1209.5 | 44.90 | 0.65 | 543.07 | 930.97 | 844.4 | 7.86 | 852.26 | 0.915 |
| 1383.1 | 45.97 | 0.65 | 635.81 | 1089.4 | 1052.2 | 8.99 | 1061.2 | 0.974 |
| 1381.6 | 46.76 | 0.65 | 646.04 | 1107.5 | 1024.7 | 8.98 | 1033.7 | 0.933 |
| 1172.2 | 46.81 | 0.65 | 548.71 | 940.64 | 844.3 | 7.62 | 851.9 | 0.906 |
| 1110.9 | 46.89 | 0.65 | 520.90 | 892.97 | 804.6 | 7.22 | 811.82 | 0.909 | from these two ports can be analyzed for soluble sulfate concentrations, specific gravities, and crystal size. The flow rates of the reactants and of the slurries are adjusted in accordance with the analytical values obtained in order to maintain the desired sulfate levels within the reaction system. It is to be understood that the system described can be run on a continuous basis, the reactants are continuously added and the third portion of the second slurry is continuously removed from the system prior to separation into phosphoric acid and calcium sulfate hemihydrate.

In FIG. I is shown a schematic of the process. Phosphoric acid at about 70° C. is added through conduit 6 and phosphate rock which is added through conduit 8 are slurried in vessel 2 which is fitted with an agitator 4. Defoamer can be added as needed through conduit 10. The temperature of slurry 11 so formed is about 92° C. and the solids content is about 30% to about 40% by weight. Slurry 11 is transferred through conduit 12 to vessel 16. Vessel 16 is fitted with an agitator (shaft 18 and propeller 21 attached to the bottom thereof), and a draft tube 20 which is secured to the inside wall of vessel 16 by braces (not shown). Slurry 11 flows into slurry 22 which is composed of calcium sulfate hemihydrate, monocalcium phosphate, phosphoric acid, and sulfuric acid. The propeller 21 of the agitator is so positioned with respect to the location of the draft tube 20 that on actuation of the shaft 18 and propeller 21 by a motor (not shown), a slurry 22 in vessel 16 will flow from the bottom portion of the draft tube 20 up through the draft tube. On exiting the top of the draft tube, slurry 22 will flow downwardly in the space between the draft tube 20 and the inside walls of vessel 16. A first portion of slurry 33 is transferred from vessel 28 through conduit 38 to vessel 16. The flow created within vessel 16 thoroughly mixes slurry 11 and slurry 33 within slurry 22. Slurry 22 is then transferred to vessel 28 through conduits 24 using pump 25. Vessel 28 may be vertically offset from vessel 16 or it may be on the same level as vessel 16. Samples for analysis of the first slurry are removed from sample port 25a. Slurry 22 is at a temperature of about 66° C. to about 113° C., and has a soluble sulfate value of about +0.7 to about −4%.

On entering vessel 28 which is equipped with an agitator (shaft 30 and propeller 31 attached to the bottom thereof), a draft tube 32 and a sulfuric acid inlet 34, slurry 22 is dispersed into slurry 33. Draft tube 32 is secured to the inside wall of vessel 28 by braces (not shown). Sulfuric acid is added from the sulfuric acid inlet 34 and is also thoroughly dispersed into slurry 33. Crystal modifier may be added to vessel 28 through an inlet not shown. Activation of the agitator (shaft 30 and propeller 31) by means of a motor (not shown) causes a flow of slurry 33 from the bottom of the draft tube 32 up through the draft tube and out the top portion of said draft tube. On exiting the top of the draft tube 32, the slurry flows downwardly in the space between the draft tube 32 and the inside walls of vessel 28. A circulation established within vessel 28 disperses slurry 22 and sulfuric acid into slurry 33, constantly renewing surface 36. Vessel 28 is subjected to a pressure of about 2 inches of mercury to about 29 inches of mercury absolute. Water is evaporated from the hot slurry thus cooling the slurry. In addition to water, other volatile materials produced by the reaction of sulfuric acid and phosphate rock are also removed. These materials include HF, $SiF_4$, $H_2S$, $SO_2$, $CO_2$ and others. Because of the internal circulation of the slurry within vessel 28 temperature gradients are minimized. Slurry 33 maintained at a temperature of about 66° C. to about 113° C., preferably from about 80° C., to about 105° C., and having a sulfate content of about $+0.7$ to about $+4.5\%$ is recirculated back to vessel 16 through conduit 38. Slurry 33 is efficiently dispersed within slurry 22 in vessel 16 by means of the internal circulation within vessel 16. Thus a system has been developed in which both inter and intra-vessel circulation occur so as to better disperse the reactants being added to the slurries and to reduce temperature gradients within the vessels due to heating and cooling.

A portion of slurry 33 about equal to the amount of reactants added (phosphoric acid, phosphate rock and sulfuric acid), minus the amount of water and volatiles removed from the system is removed from vessel 28 through conduit 40. Samples for analysis of the second slurry are removed from sample port 41 located on conduit 40. The slurry is pumped (pump not shown) to reservoir 44 from which it flows to vessel 48 through conduit 46. Agitator 50 maintains the slurry in a dispersed condition in vessel 48. The slurry is pumped (pump not shown) from vessel 48 through conduit 52 to the separation section (not shown).

Reactants are continuously added to vessel 16 and 28 with water and volatiles and the product slurry constantly being withdrawn from vessel 28. In case of a separation apparatus breakdown the system can be placed on recycle. No reactants would be added to the system. Intra-vessel circulation would continue and inter vessel circulation would be discontinued.

It is to be recognized that the elevation of vessels 2, 16, 28, 44 and 48 with respect to each other may be varied without affecting the instant invention. Likewise, the conduits connecting vessels 2, 16, 28, 44 and 48 may be rearranged, additional conduits added and/or existing conduits deleted without affecting the instant invention. For example, slurry 22 passing from vessel 16 to vessel 28 may be introduced into the top part of vessel 28 rather than the bottom part without affecting the instant invention.

Another embodiment of the claimed invention is shown in FIG. II. Instead of adding the reactants phosphoric acid, phosphate rock and if necessary, the defoamer to a preslurry vessel 2 as shown in FIG. I, the reactants are added directly to the first slurry 22 in vessel 16. The phosphoric acid is added through conduit 7 and the phosphate rock is added through conduit 9. The reactants are added in amounts such that the direct combination of the two results in a slurry containing between about 30% to about 40% solids by weight and an initial concentration of about 13% to about 47% $P_2O_5$ in the liquid portion of the slurry. Defoamer is added through conduit 13, if, and when needed. Once the reactants are dispersed in the first slurry 22, the parameters such as temperatures, pressures, concentrations, and flows are the same as described above for the more preferred embodiment.

FIG. III shows the flow or circulation patterns of the slurry in the system of the instant invention. Slurry 60 flows from vessel 61 through conduit 62 into vessel 63. Vessel 63 is fitted with a draft tube 64 and an agitator 65. Slurry 65a flows within vessel 63 as shown by dotted lines 66. Conduits 67, 68, and 69 are used to circulate slurries, 65a and 72a between vessel 63 and 70 respectively. Slurry 65a flows through conduits 67 and 68 into vessel 70, said vessel being fitted with a draft tube 71 and an agitator 72 and a sulfuric acid inlet 74 for sulfuric acid introduction into slurry 72a. Slurry 72a flows within vessel 70 as shown by dotted lines 73. It should be recognized that the direction of flows shown by dotted lines 66 and 73 can be reversed without disrupting the process. A flow or circulation pattern is established between vessels 63 and 70 through conduits 67, 68 and 69 respectively. Of equal importance are the flow patterns established within vessel 63 and within vessel 70. The flow pattern of slurry within vessel superimposed upon the flow patterns of slurry between vessels results not only in excellent dispersion of reactants within the slurry but also maintenance of very low temperature differentials within a given vessel.

EXAMPLE

Vessels 16 and 28 and the accompanying connective means such as conduits, pumps, etc. of FIG. I are filled with a slurry consisting of calcium sulfate hemihydrate, monocalcium phosphate, phosphoric acid and sulfuric acid. The weight percent of the solids in the slurry is about 31%, the specific gravity of the slurry in vessel 28 is about $1.80 \pm 0.07$ g/cc and the specific gravity of the liquid portion of the slurry is about $1.53 \pm 0.06$ g/cc. $P_2O_5$ concentration of the liquid portion of the slurry is about 42% by weight. The temperature of the slurry in vessel 16 is between about 88°–102° C. preferably between 92° C. and 105° C., whereas the temperature in vessel 28 is between 88° and 105° C., preferably between 92° C. and 105° C. Soluble sulfate concentration in vessel 16 is from about $+0.7$ to about $-4\%$ and the soluble sulfate concentration in vessel 28 is from about 0.7% to about $+4.5\%$.

A mixture of phosphate rock (typical analysis shown in Table 2) of a size distribution shown in Table 3, and phosphoric acid is prepared by adding phosphate rock to phosphoric acid in the ratio of about 1647 pounds of phosphate rock (about 31.2 $P_2O_5$ and 45.6 CaO) to about 3700 pounds of phosphoric acid (about 32% $P_2O_5$). The temperature of the mixture is about 90° C. A tall oil sulfonic acid defoaming agent is added as needed to reduce the foam caused by partial dissolution of the phosphate rock in phosphoric acid.

This phosphate rock-phosphoric acid mixture is added to the first slurry in vessel 16 at the rate of about 380 gpm (about 5350 pounds per minute). The incoming mixture is thoroughly mixed with the first slurry and a first portion of the second slurry from the second reaction vessel. Intra vessel mixing is accomplished by means of the draft tube and the agitator. The first slurry is pumped from the first reaction vessel 16 to the second reaction vessel 28 at the rate of about 1640 gallon per minute. The first slurry is thoroughly mixed with the second slurry and 98% sulfuric acid which is added to the second reaction vessel at about 87 gpm. An organic sulfonic acid derivative can be added to the second reaction vessel 28. This material is added to promote the growth of the hemihydrate crystals. The first slurry, the sulfuric acid and the crystal modifier are thoroughly dispersed into the second slurry in the second reaction vessel 28. The second slurry flows at the rate of aboue 1280 gallons per minute from vessel 28 into vessel 16 where it is thoroughly mixed with the first slurry.

About 45 gpm of water and volatile materials (HF, $SiF_4$, $H_2S$, $CO_2$ etc.) is vaporized from the second slurry in vessel 28. Vessel 28 is maintained under a vacuum of about 15 inches of mercury absolute. Approximately 400 gpm of slurry is withdrawn from the second reaction vessel and flows to vessel 48, the separator feed tank. Thus about 445 gpm of material (vaporized material and the slurry to the separator feed tank) is removed from the system. The removed slurry is then passed to the separation section where the solid and liquid portions of the slurry are separated.

At these rates, the plant will produce about 350 tons per day of $P_2O_5$ of 35-44% $P_2O_5$ phosphoric acid. The recovery data is summarized below.

| TOTAL LOSS IN FILTER CAKE | |
| --- | --- |
| | % of $P_2O_5$ fed in rock |
| Citrate insoluble (CI) | 0.76 |
| Citrate soluble (CS) | 4.64 |
| Water soluble (WS) | 2.34 |
| Total loss | 7.74 |
| Total Recovery | 92.26 |

A typical analysis of the phosphoric acid produced by this process is shown in Table 4. The total residence time, from entering vessel 16 to exiting vessel 48, is calculated at 7.9 hours. The volume of vessel 16 is about 120,000 gallons, the volume of vessel 28 is about 40,000 gallons to normal liquid level.

Phosphate rock is present in the first and in the second slurries in the first and second reaction vessels respectively. The amount present is quite small and will vary considerably. The value for the "Citrate Insoluble" loss of the filter cake is a rough measure of undissolved and unreacted phosphate rock.

Table 2

| Typical Phosphate Rock Analysis | |
| --- | --- |
| Compound | % By Weight |
| $P_2O_5$ | 31.2 |
| CaO | 45.6 |
| $Fe_2O_3$ | 1.4 |
| $Al_2O_3$ | 1.2 |
| MgO | 0.4 |
| $SiO_2$ | 8.7 |
| F | 3.7 |
| $SO_3$ | 0.9 |
| $CO_2$ | 3.6 |
| Organic | 1.8 |
| $H_2O$ | 1.1 |

Table 2-continued

| Typical Phosphate Rock Analysis | |
| --- | --- |
| Compound | % By Weight |
| $Na_2O$, $K_2O$ | 0.4 |

Table 3

| Typical Phosphate Rock Screen Analysis | |
| --- | --- |
| Mesh | Cummulative Percent |
| +14 | 0.4 |
| +24 | 2.6 |
| +28 | 9.3 |
| +35 | 26.6 |
| +48 | 64.1 |
| +65 | 86.4 |
| +100 | 97.7 |
| −100 | 2.3 |

Table 4

| Typical Phosphoric Acid Analysis | |
| --- | --- |
| $P_2O_5$ | 37.95 |
| $SO_4^=$ | 1.72 |
| CaO | 1.04 |
| $F^-$ | 1.27 |
| MgO | 0.46 |
| $Fe_2O_3$ | 0.97 |
| $Al_2O_3$ | 0.91 |

What is claimed is:

1. A process for the preparation of phosphoric acid from phosphate rock and sulfuric acid comprising the steps of:

(a) adding phosphate rock and phosphoric acid to a first reaction vessel which contains a first slurry comprising calcium sulfate hemihydrate, monocalcium phosphate, and phosphoric acid, whereby the added phosphate rock is substantially converted to monocalcium phosphate, calcium sulfate hemihydrate, and phosphoric acid while maintain the first slurry at a soluble sulfate concentration of about +0.7 to about −4% and at a temperature of about 66% to about 113° C. and $P_2O_5$ concentration such that the calcium sulfate by product is the hemihydrate;

(b) adding sulfuric acid in amounts such that the sulfate content of the sulfuric acid plus the sulfate content of the added phospate rock is equivalent to about 90% to about 100% of the stoichiometric amount of sulfate required to react with the calcium present in the phosphate rock added in part (a) to form calcium sulfate hemihydrate to a second reaction vessel maintained at a reduced pressure of about 3 to about 20 inches of mercury absolute and a temperature of about 66°-113° C. which contains a second slurry comprising calcium sulfate hemihydrate, monocalcium phosphate, sulfuric acid and phosphoric acid, whereby the sulfuric acid reacts with the monocalcium phosphate and the phosphate rock to form calcium sulfate hemihydrate and phosphoric acid, said second slurry being maintained at a soluble sulfate concentration of about 0.7% to +4.5 %, provided that the soluble sulfate content of the second slurry is about +1.0% or greater when the soluble sulfate content of the first slurry is about +0.7;

(c) circulating a first portion of the first slurry from the first reaction vessel through a first conduit into the second reaction vessel and circulating a first portion of the second slurry from the second reaction vessel through a second conduit into the first reaction vessel, the circulation being continuous;

(d) circulating a second portion of the first slurry within the first reaction vessel and circulating a second portion of the second slurry within the second reaction vessel, through a draft tube in each case, at a rate at least equal to 50% of the volume of the slurry in the vessel per minute to better mix the slurries in both the first and second reaction vessels; and (e) separating a third portion of the second slurry into a liquid, comprising phosphoric acid, and a solid comprising calcium sulphate hemihydrate.

2. The process as recited in claim 1 in which a defoaming agent is added to the first slurry in the first reaction vessel.

3. The process as recited in claim 2 in which a reagent which increases the growth of the calcium sulfate hemihydrate crystals is added to the second reaction vessel.

4. The process as recited in claim 1 in which the second slurry in the second reaction vessel has a slurry specific gravity of between about 1.58 to about 1.99 grams/cc, the liquid portion of said slurry has a specific gravity of from about 1.36 to about 1.72 grams/cc.

5. The process as recited in claim 1 in which a reagent which increases the growth of the calcium sulfate hemihydrate crystals is added to the second reaction vessel.

6. The process as recited in claim 1 in which the soluble sulfate concentration of the first slurry in the first reaction vessel is from about −1% to about −3%, the soluble sulfate concentration of the second slurry in the second reaction vessel is from about +2.25% to about 3.25%.

7. The process as recited in claim 1 in which, the specific gravity of the slurry is from about 1.58 to about 1.99 grams/cc, the specific gravity of the liquid portion of the slurry is from about 1.36 to 1.72 grams/cc, the $P_2O_5$ content of the liquid portion of the slurry is from about 30% to about 55% by weight, and the soluble sulfate content of the liquid portion of the slurry is from about 2.25% to about 3.25%.

8. The process as recited in claim 1 in which the phosphoric acid added to the first reaction vessel in step (a) contains from about 0.5% to about 3.5% sulfuric acid by weight.

9. A process for the preparation of phosphoric acid from phospate rock and sulfuric acid comprising the steps of:

(a) adding the phosphate rock and phosphoric acid in the ratio of about 165 parts of phosphate rock to about 240 to about 390 parts of phosphoric acid containing from about 13% to about 47% $P_2O_5$ by weight and from about 0.5% to about 3.5% $H_2SO_4$ by weight to a first reaction vessel which contains a first slurry comprising calcium sulfate hemihydrate, monocalcium phosphate, and phosphoric acid, said vessel being maintained at a temperature of about 66° to about 113° C. and $P_2O_5$ concentration such that the calcium sulfate by product is the hemihydrate, whereby the added phosphate rock is substantially converted to monocalcium phosphate, calcium sulfate hemihydrate, and phosphoric acid while maintaining the first slurry at a soluble sulfate concentration of about +0.7 to about −4%;

(b) adding sulfuric acid in amounts such that the sulfate content of the added phosphate rock is equivalent to about 90% to about 100% of the stoichiometric amount of sulfate required to react with the calcium present in the phosphate rock added in part (a) to form calcium sulfate hemihydrate to a second reaction vessel which contains a second slurry comprising calcium sulfate hemihydrate, monocalcium phosphate, and phosphoric acid, whereby the sulfuric acid is added and reacts with the monocalcium phosphate and the phosphate rock to form calcium sulfate hemihydrate and phosphoric acid, said second slurry being maintained at a soluble sulfate concentration of about 0.7% to +4.5%, provided that the soluble sulfate content of the second slurry is about +1.0% or greater when the soluble sulfate content of the first slurry is about +0.7%, the slurry has a specific gravity of between about 1.58 to about 1.99 grams/cc, the specific gravity of the liquid portion of the slurry has a specific gravity of from about 1.36 to about 1.72 grams/cc;

(c) circulating a first portion of the first slurry from the first reaction vessel through a first conduit into a second reaction vessel maintained at a reduced pressure of about 3 to about 20 inches of mercury absolute and a temperature of about 66° to about 113° and circulating a first portion of the second slurry from the second reaction vessel through a second conduit into the first reaction vessel, the rate of circulation being such that the sulfate levels are maintained from about +0.7% to about −4% in the first reaction vessel and from about +0.7% to about +4.5% in the second reaction vessel, provided that the soluble sulfate content of the second slurry is about 1.0% or greater when the soluble sulfate content of the first slurry is about +0.7%, the circulation being continuous;

(d) circulating a second portion of the first slurry within the first reaction vessel and circulating a second portion of the second slurry within the second reaction vessel, through a draft tube in each case, at a rate at least equal to 50% of the volume of the slurry in the vessel per minute to better mix the slurries in both the first and second reaction vessels; and (3) separating a third portion of the second slurry into a liquid comprising phosphoric acid and a solid comprising calcium sulphate hemihydrate.

* * * * *